United States Patent [19]  
Michl et al.

[11] Patent Number: 4,629,746  
[45] Date of Patent: Dec. 16, 1986

[54] RADIOPAQUE DENTAL MATERIALS

[75] Inventors: Rudolf J. Michl, Schaan; Volker M. Rheinberger, Vaduz; Gilbert Ott, Schaan, all of Liechtenstein

[73] Assignee: Etablissement Dentaire Ivoclar, Schaan, Liechtenstein

[21] Appl. No.: 747,176

[22] Filed: Jun. 21, 1985

[30] Foreign Application Priority Data

Jan. 26, 1985 [DE] Fed. Rep. of Germany ....... 3502594

[51] Int. Cl.<sup>4</sup> ............................... A61K 6/08
[52] U.S. Cl. ................... 523/117; 433/228.1; 523/116
[58] Field of Search ............................ 523/116, 117; 433/228.1, 199.1, 201.1

[56] References Cited

U.S. PATENT DOCUMENTS 3,826,778  7/1974  Dietz ................... 523/117
3,971,754  7/1976  Jurecic ................. 523/117
4,302,376  11/1981  Walkowiak et al. ..... 523/117

Primary Examiner—Lorenzo B. Hayes  
Attorney, Agent, or Firm—Cushman, Darby & Cushman

[57] ABSTRACT

Apart from polymerizable organic binders, a radiopaque dental material contains a fluoride of the rare earth metals or mixtures of such fluorides, as well as optionally further inorganic compounds as fillers. The dental material is suitable as a one or two-component filling material for dental cement, as a crown and bridge material, as well as for producing dentures, inlays and implants and is characterized by a high radiopacity and at the same time a good transparency.

14 Claims, 3 Drawing Figures

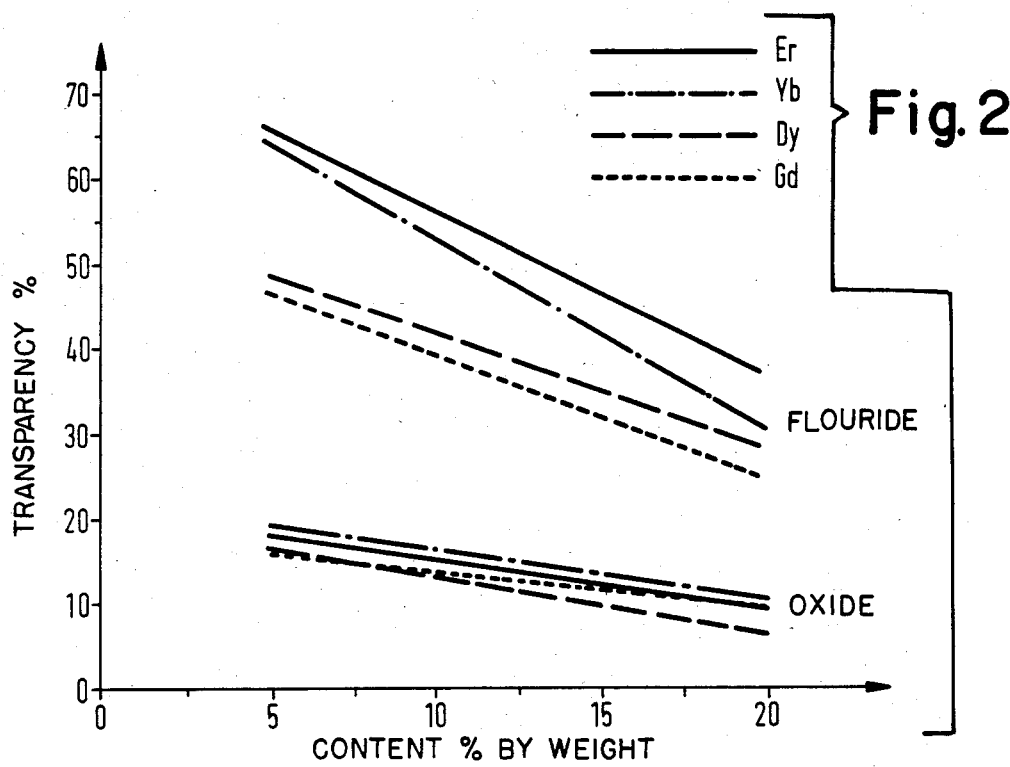
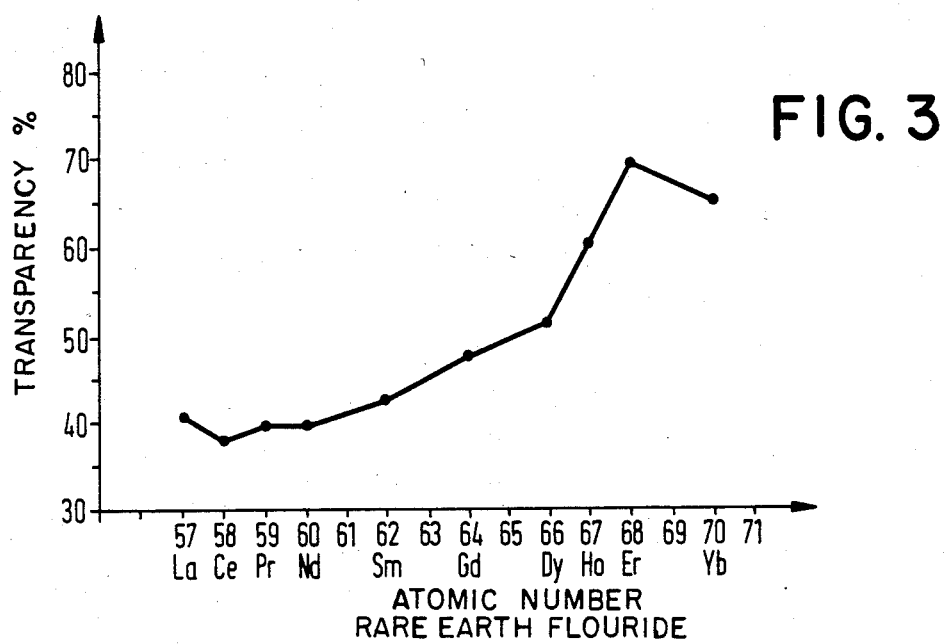

RADIOPAQUE DENTAL MATERIALS

The invention relates to radiopaque dental materials, such as e.g. filling materials, dental cements, crown and bridge materials, prosthesis materials, as well as the use thereof for producing dentures, inlays, implants and finished parts. Prothesis materials thus include denture based materials.

BACKGROUND OF THE INVENTION

DE-OS No. 2,458,380 discloses dental filling materials which contain oxides and/or carbonates of lanthanum, hafnium, strontium and/or tantalum as radiopaque fillers. This publication also discloses that it is known that elements with a high atomic weight have a stronger X-ray absorption. However, there are limits to the uses thereof in the vicinity of the human tissue, because many of these heavy elements are toxic or radioactive.

DE-OS No. 2,420,531 also discloses dental filling materials, which can contain as radiopaque material barium sulphate, tantalum, iodalphionic acid, iopanionic acid or ipodoic acid. Reference is also made to the other radiopaque materials described in Kirk-Othmer, Encyclopedia of Chemical Technology, 2nd edition, Vol. 17, pp. 130–141.

European Pat. No. 11,735 describes dental filling materials containing as the contrast medium compounds of barium, bismuth, lanthanum, thorium and rare earth metals, preference being given to the use of barium sulphate.

It is known from other publications to incorporate methacrylate particles of aliphatic halogen compounds, such as e.g. tetrabromomethane, bromoform, ethyl iodide, iodobenzene, etc. This is brought about by suspension polymerization of an alkyl methacrylate. There can be an adhesive pigment of a heavy metal compound on the beads for increasing the radiopacity.

The literature also mentions dental materials, which e.g. contain tin compounds, barium glasses, barium sulphate, etc as the radiopaque agent. A description is also provided of glass ceramics containing lanthanum, zirconium, strontium, tantalum or hafnium in the form of their oxides, carbonates or fluorides. It is stated in DE-OS No. 2,935,810, that although oxides of rare earths (elements 57 to 71) have been proposed as impervious to X-rays, but problems then occur due to undesired discolouration.

It has also already been proposed to use calcium, strontium, barium, lanthanum, rare earths, tantalum and/or hafnium aluminosilicate with a zeolite structure as the filler for a dental material.

In addition, radiopaque filling materials are known, whose filler consists of a mixture of microfine silicon dioxide and radiopaque glasses, the latter having an average particle size over 1 $\mu$m. All the hitherto known radiopaque microfilled dental materials suffer from the disadvantage that the radiopacity is still unsatisfactory. In addition, the transparency of the known radiopaque microfilled dental materials is unsatisfactory and the high-lustre polishability inadequate.

SUMMARY OF THE INVENTION

The problem of the present invention is consequently to provide a microfilled dental material having a good radiopacity and at the same time a good transparency, whilst there is no deterioration of the physical characteristics and which has a good abrasion behaviour and simultaneous good polishability to high lustre.

The invention relates to a dental material according to the claims.

It has surprisingly been found that the use of fluorides of rare earth metals in dental materials leads to the aforementioned advantageous characteristics. Fluoride ions released from the dental material have also a beneficial anti-caries effect. This refers to trifluorides of elements 57 to 71. Although these fluorides are known as compounds per se, it was surprising that they have a greatly improved transparency and are less soluble in the mouth compared with oxides of rare earth metals, no reference being made to this in the literature.

In particular, the fluorides of rare earth metals with atomic numbers 59 to 71 have proved usable, the preferred compounds being those of elements 66 to 71. Ytterbium fluoride is used with particular preference.

Fluorides of rare earth metals are generally incorporated into the dental material in powder form. The average primary particle size can vary and in the case of a microfilled dental filling material it is in the range 5 to 700, particularly 20 to 500 and especially 50 to 300 nm. Optionally, the average primary particle size can be in the range 700 nm to 5 $\mu$m.

The rare earth metal fluoride content, based on the total weight is between 1 and 50%, particularly between 5 and 40% and more especially between 10 and 25%. It is in particular dependent on the desired radiopacity and/or transparency. It is also possible to use mixtures of rare earth metal fluorides.

DETAILED DESCRIPTION OF THE INVENTION

Figure 1:
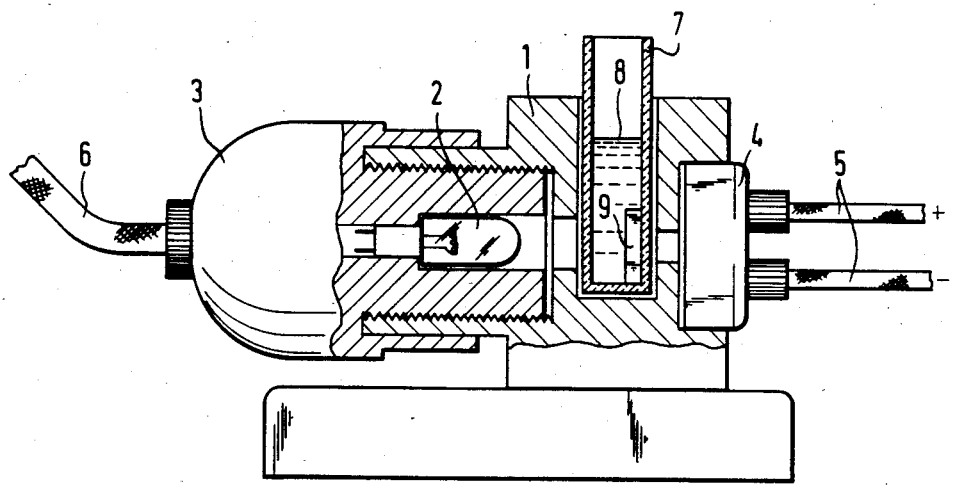

The dental material conventionally contains other non-radiopaque, inorganic constituents. Suitable fillers are e.g. amorphous silica, particularly pyrogenic and precipitated silica with a BET surface of approximately 20 to 400 m$^2$/g. In particular, pyrogenic silica with a BET surface of 30 to 300 m$^2$/g and an average primary particle size of approximately 5 to 50 nm are used, particular preference being given to materials in the range between 12 to 50 nm. Silica with an average primary particle size of 50 to 1000, preferably 100 to 300 nm can also be used.

The quantity of non-radiopaque fillers in the dental material is dependent on the quantity of rare earth metal fluorides used and generally is in the range 5 to 84%, particularly 10 to 70% and more especially 20 to 50%. In all, the content of fillers (rare earth metal fluorides and further inorganic compounds) is 6 to 85, preferably 15 to 85 and more especially 30 to 85% by weight.

The rare earth metal fluorides and in particular the additional inorganic constituents of the dental material can be silanized in the usual way, in order to improve the bond between the organic matrix and the inorganic filler. For example, $\gamma$-methacryloxypropyltrimethoxysilane is suitable as bonding agent. The quantity of anchoring agent used depends on the nature of the filler and the desired viscosity of the dental material.

In addition, the dental material must contain a polymerizable vinyl compound. Monofunctional or polyfunctional methacrylates, which can be used alone or in mixtures are particularly suitable. Examples of these compounds are methyl methacrylate, isobutyl methacrylate, cyclohexyl methacrylate, triethylene glycol dimethacrylate, diethylene glycol dimethacrylate, ethylene glycol dimethacrylate, polyethylene glycol dimethacrylate, butane diol dimethacrylate, hexane diol dimethacrylate, decane diol dimethacrylate, dodecanol diol dimethacrylate, bisphenol A-dimethacrylate, trimethylol propane dimethacrylate, but it is also possible to consider bis-GMA, together with reaction products of isocyanate, particularly diisocyanates and/or triisocyanates and OH group-containing methacrylates. Examples are the reaction products of 1 mol of hexamethyldiisocyanate and 2 mol of 2-hydroxyethylene methacrylate, of 1 mol of tri-(6-isocyanotohexyl)-biuret and 3 mol of hydroxyethyl methacrylate, as well as 1 mol of trimethyl hexamethylene diisocyanate and 2 mol of hydroxy ethyl methacrylate, referred to hereinafter as urethane dimethacrylate. The proportion of these mainly long-chain compounds in the dental material is between 10 and 50% by weight. In principle, it is possible to use all binders usable for a dental material. As a function of the nature of the catalyst used, the dental material can be cured hot, cold or by photopolymerization.

The catalysts for hot polymerization can be constituted by known peroxides, such as dibenzoyl peroxide, dilauroyl peroxide, tert-butyl peroctoate or tert-butyl perbenzoate, but α,α-azo-bis-(isobutyroethylester), benzpinacol and 2,2'-dimethylbenzpinacol are also suitable.

Benzophenone and its derivatives, as well as benzoin and its derivatives are suitable as catalyst for photopolymerization. Also examples of preferred photosensitizers are α-diketones, such as 9,10-phenanthrenequinone, diacetyl, furil, anisil, 4,4'-dichlorobenzil and 4,4'-dialkoxybenzil, camphor quinone being used with particular preference. Preference is given to the use of photosensitizers, together with a reducing agent. Examples of reducing agents are amines, such as cyanoethyl methyl aniline, dimethylaminoethyl methacrylate, n-butylamine, triethylamine, triethanolamine, N,N'-dimethylaniline, N-methyldiphenylamine and N,N-dimethyl-sym-xylidine.

The catalysts used for cold polymerization are radical-supplying systems, e.g. benzoyl or lauroyl peroxide, together with amines such as N,N-dimethyl-sym-xylidine or N,N-dimethyl-p-toluidine.

The quantity of said catalysts in the dental material is normally between 0.1 and 5% by weight.

It is also possible to incorporate into the dental material finely divided splinter or bead polymers, which can be homopolymers or copolymers of the aforementioned vinyl compounds. These homopolymers or copolymers can in turn be filled with the aforementioned inorganic fillers, including those of a radiopaque nature. In this connection, reference is made to European Pat. No. 11,190 and German Pat. No. 2,403,211. The dental material can also contain conventional pigmenting agents and stabilizers.

The dental material according to the invention is preferably used as a dental filling material. The intention is that, when preparing the X-ray pictures, the dentist will be put into the position of being able to establish whether or not secondary caries have formed, as a result of the radiopacity of the filling. A light-hardening, radiopaque filling material e.g. contains as the binder a urethane dimethacrylate or bis-GMA, triethylene glycol dimethacrylate as the diluting monomer, rare earth metal fluorides, e.g. ytterbium trifluoride, pyrogenic silica with an average primary particle size of 40 nm and a BET surface of 50 m$^2$/g, camphor quinone and N,N-dimethyl-sym-xylidine as the catalyst, together with stabilizers and dye pigments.

In order to increase the degree of filling of such filling materials, it is of a standard nature to produce a copolymer, e.g. from bis-GMA, triethylene glycol dimethacrylate, ytterbium fluoride and pyrogenic silica, to grind the same as a splinter polymer and then incorporate it into the filling material. After making the filling, polymerization takes place by means of a commercial halogen lamp.

Dental filling materials are also produced as two-component materials, which cure cold after mixing. The composition is much the same as for the light-hardening materials, except that the instead of the photocatalyst a catalyst such as benzoyl peroxide is mixed into one paste and e.g. N,N-dimethyl-p-toluidine is mixed into the other paste. Through mixing roughly equal amounts of the two pastes, a dental filling material is obtained, which cures or hardens in a few minutes.

If the amine is omitted from the latter materials and e.g. only benzoyl peroxide is used as the catalyst, a hot-hardening dental material is obtained, which can be used for producing an inlay for dentures. An impression is taken of the cavity in the mouth for the purpose of producing an inlay and then a gypsum model is produced. The paste is introduced into the gypsum model cavity and the complete entity is polymerized in a pressure pot under the action of heat. The inlay is removed, worked and then cemented into the cavity in the patient's mouth.

The invention not only relates to radiopaque dental material, but also to the finished parts produced therefrom, e.g. dentures, plates, inlays, etc. It is illustrated by means of the following examples.

EXAMPLE 1

Pastes with the following composition were prepared. X% by weight of rare earth metal fluoride (REF$_3$). 70-X% by weight SiO$_2$ (Aerosil OX 50 of Degussa AG)-silanized.

24% by weight urethane dimethacrylate.
5% by weight decamethylene dimethacrylate.
1% by weight benzoyl peroxide.

REF$_3$ is a general formula for the specific fluorides identified in TABLE I.

The specimens of 1×10×12 mm are produced by polymerization under pressure at 120° C. for the transparency measurements and 2×2×25 mm for measuring the radiopacity.

The transparency measurement takes place with the transparency testing device shown in FIG. 1. The test specimen 9 is placed in a glass flask 7 filled with water 8, whereby it engages on the flask wall, which is terminated against the photoelectric cell 4. The flask is surrounded by base 1. Photoelectric cell 4 is connected via connections 5 to a measuring device. The zero calibration of the measuring device takes place automatically without light (light source 2 in the lamp housing 3 switched off), whilst the 100% calibration takes place without the test specimen and with light (light source 2 switched on). The light source is supplied via cable 6 by means of a 4 Volt transformer with an incorporated voltage stabilizer.

The radiopacity is measured in the following way. An aluminium stop wedge (purity>99.5%) of length 25 mm and width 15 mm is produced, with steps at 1, 2, 3, 4 and 5 mm.

An X-ray film (ISO 3665, Kodak, Ektaspeed/Phil-X-Film) was placed on a lead plate (thickness>2.0 mm). The test specimen and aluminium stop wedge were juxtaposed in the centre of the film. The complete entity was then irradiated with a dental X-ray lamp, 70 kV Transdent D502 with diameter 6 cm$^3$) at 70 kVp from a distance of 100 mm, for 0.3 seconds at 12 mA. After developing the film, the density caused by the test specimen was visually compared with that of the aluminium test specimen. The radiopacity RO at % Al is calculated:

$$RO = I_{Al}/I_p \cdot 100 \ (\% \ Al)$$

$I_p$ = test specimen thickness
$I_{Al}$ = aluminium wedge thickness with the same density as the test specimen.

Table I gives the values. It can be seen that the transparency increases as the rare earth metal fluoride percentage decreases, whilst the opposite applies with regards to the radiopacity.

Table II shows the transparency and radiopacity as a function of the rare earth metal oxide content.

TABLE I

| Rare earth metal fluoride | % by weight in paste | Transparency a % | Radiopacity in % Al (visual) |
|---|---|---|---|
| LaF$_3$ | 5 | 41 | 50 |
|  | 10 | — | — |
|  | 15 | — | — |
|  | 20 | 23 | 175 |
| CeF$_3$ | 5 | 38 | 75 |
|  | 10 | — | — |
|  | 15 | — | — |
|  | 20 | 17 | 200 |
| SmF$_3$ | 5 | — | 70 |
|  | 10 | — | — |
|  | 15 | — | — |
|  | 20 | 29 | 175 |
| GdF$_3$ | 5 | 48 | 70 |
|  | 10 | 39 | 100 |
|  | 15 | 33 | 150 |
|  | 20 | — | — |
| DyF$_3$ | 5 | 52 | 75 |
|  | 10 | 40 | 100 |
|  | 15 | 35 | 150 |
|  | 20 | 30 | 200 |
| ErF$_3$ | 5 | 70 | 75 |
|  | 10 | 54 | 125 |
|  | 15 | 46 | 159 |
|  | 20 | 38 | 200 |
| YbF$_3$ | 5 | 66 | 70 |
|  | 10 | 53 | 125 |
|  | 15 | 43 | 175 |
|  | 20 | 31 | 225 |

— Value not measured

TABLE II

Transparency and radiopacity as a function of rare earth metal oxide content

| Rare earth metal oxide | % by weight in paste | Transparency as % | Radiopacity in % Al |
|---|---|---|---|
| Gd$_2$O$_3$ | 5 | 16 | |
|  | 7.5 | 15 | |
|  | 10 | 13 | |
|  | 15 | 11 | |
|  | 20 | 9 | |
| Dy$_2$O$_3$ | 5 | 18 | |
|  | 7.5 | 18 | |
|  | 10 | 11 | |
|  | 15 | 8 | |
|  | 20 | 8 | |
| Er$_2$O$_3$ | 5 | 21 | |
|  | 7.5 | 16 | |
|  | 10 | 13 | |
|  | 15 | 11 | |
|  | 20 | 11 | |
| Yb$_2$O$_3$ | 5 | 21 | 75 |
|  | 7.5 | 15 | 100 |
|  | 10 | 14 | 150 |
|  | 15 | 13 | 200 |
|  | 20 | 11 | 225 |

FIG. 2 gives the transparency as a function of the rare earth metal oxide and fluoride content.
(X% RE$_2$O$_3$ or REF$_3$, 70-X% Aerosil (OX 50) silanized
24% urethane dimethacrylate
5% decamethylene dimathacrylate
1% benzoyl peroxide (50% in phthalate).

FIG. 3 shows the transparency of rare earth metal fluorides according to their atomic number in the dental material of example 1 using the data from Table 1 at 5 wt. % REF$_3$ content.

EXAMPLE 2

A dental material according to the invention with the following composition was produced:
20% by weight ytterbium trifluoride
50% by weight silanized amorphous SiO$_2$ (BET surface 50 m$^2$/g; Aerosil OX50 of Degussa AG)
24% by weight urethane dimethacrylate
5.3% by weight triethylene glycol dimethacrylate
0.1% by weight camphor quinone
0.2% by weight N,N-dimethyl-sym-xylidine
0.4% by weight dye pigments and stabilizers.

The components were homogeneously mixed in a kneader, this being facilitated by slight heating. Metal abrasion is prevented by suitable coating of the metal parts of the kneader.

The paste obtained is eminently suitable as a dental filling material. It hardens completely on irradiation with light in a very short time. It can e.g. be produced and stored in black syringes. The radiopacity is excellent, as is the tooth-like transparency, the high-lustre polishability and the solubility behaviour in the mouth. The latter is understood to mean a low solubility of the fillers or filling in the saliva.

EXAMPLE 3

A two-component dental filling material was prepared as follows:

|  | Peroxide paste | Amine paste |
|---|---|---|
| 1. Bis-GMA | 20.4% | 20.4% |
| 2. Triethylene glycol dimethacrylate | 10.6% | 10.6% |
| 3. Ytterbium trifluoride | 15% | 15% |
| 4. Silanized amorphous SiO$_2$ (BET 50 m$^2$/g) | 20% | 20% |
| 5. Prepolymer of 1–4 | 32.6% | 32.7% |
| 6. Benzoyl peroxide | 1.3% | — |
| 7. N,N—diethanol-p-toluidine | — | 1,2% |
| 8. Dye pigments and stabilizers | 0.1% | 0.1% |

Prepolymer 5 comprises:
20% No. 3
50% No 4
22% No 1
8% No 2.

Peroxide paste and amine paste in equal parts where thoroughly mixed for approximately 20 seconds on a mixing block using a spatula. The paste was suitable as a dental filling material and had a good radiopacity, transparency, high-lustre polishability and solubility behaviour in the mouth.

EXAMPLE 4

A dental material according to the invention was prepared as follows:

20% dysprosium trifluoride
30% silanized amorphous silica (BET 130 m²/g; AEROSIL 130 of Degussa AG)
17% bis-GMA
15% triethylene glycol dimethacrylate
17% urethane dimethacrylate
0.5% benzoyl peroxide
0.5% dye pigments and stabilizers.

The components were homogeneously mixed to a paste in a kneader. This paste was suitable for the production of plastic inlays, whilst dentures could also be produced therefrom.

Here again, the radiopacity, transparency, solubility behaviour in the mouth and other physical characteristics were completely satisfactory.

We claim:

1. In radiopaque dental material compositions composed of an organic matrix of a polymerizable vinyl compound inorganic filler and radiopaque component; the improvement consisting essentially of, as the radiopaque component, from 1 to 50 wt. %, based on the total weight of the composition, of a rare earth metal fluoride, or mixtures of such fluorides, wherein said metal has an atomic number of from 57 to 71.

2. Dental material according to claim 1, wherein the rare earth metal has an atomic number of 66 to 71.

3. Dental material according to claim 1, wherein the rare earth metal fluoride is ytterbium trifluoride.

4. Dental material according to claim 1, wherein the inorganic filler is precipitated or pyrogenic silica with a BET surface of about 20 to 400 m²/g and an average primary particle size of about 5 to 50 mm.

5. Dental material according to claim 4, wherein the silica is present in a quantity of about 5 to 84% by weight, based on the total weight.

6. Dental material according to claim 1, wherein the inorganic fillers and radiopaque component are present in a total quantity of about 6 to 85% by weight, based on the total weight.

7. The composition of claim 1 wherein the rare earth metal fluoride is incorporated in powder form having a size between 5 to 700 nm.

8. A composition according to claim 7 wherein said particle size ranges from 20 to 500 nm.

9. The composition of claim 7 wherein said particle size range is from 50 to 300 nm.

10. The composition according to claim 7 wherein said rare earth metal fluoride content is between 5 and 40 wt. %.

11. The composition according to claim 8 wherein said rare earth metal fluoride content is between 10 and 25 wt. %.

12. The composition according to claim 1 wherein the inorganic filler is present in an amount from 5 to 84 wt. %.

13. The composition according to claim 1 wherein said inorganic filler is present in a weight range from 10 to 70 wt. %.

14. The composition according to claim 1 wherein said polymerizable vinyl compound is selected from the group consisting of methyl methacrylate, isobutyl methacrylate, cyclohexyl methacrylate, triethylene glycol dimethacrylate, diethylene glycol dimethacrylate, ethylene glycol dimethacrylate, polyethylene glycol dimethacrylate, butane diol dimethacrylate, hexane diol dimethacrylate, decane diol dimethacrylate, duodecanol diol dimethacrylate, bisphenol A-dimethacrylate, and trimethylol propane dimethacrylate.

* * * * *